(12) United States Patent
Hudkins et al.

(10) Patent No.: US 7,563,464 B1
(45) Date of Patent: Jul. 21, 2009

(54) TREATMENT OF MUCOSAL MEMBRANES UTILIZING PHYTOESTROGEN

(76) Inventors: Bruce Eric Hudkins, 1723 S. Madison Ave., Tulsa, OK (US) 74120; Thomas G. Matkov, 438 Park La., Lake Bluff, IL (US) 60044

( * ) Notice: Subject to any disclaimer, the term of this patent is extended or adjusted under 35 U.S.C. 154(b) by 0 days.

(21) Appl. No.: 11/929,086

(22) Filed: Oct. 30, 2007

Related U.S. Application Data

(62) Division of application No. 11/379,683, filed on Apr. 21, 2006, now abandoned.

(60) Provisional application No. 60/594,601, filed on Apr. 22, 2005.

(51) Int. Cl.
*A01N 65/00* (2006.01)
*A61K 36/48* (2006.01)
*A61F 13/00* (2006.01)

(52) U.S. Cl. .................. 424/725; 424/757; 424/434

(58) Field of Classification Search .................. None
See application file for complete search history.

(56) References Cited

U.S. PATENT DOCUMENTS

| | | | | |
|---|---|---|---|---|
| 6,017,520 | A * | 1/2000 | Synodis et al. | 424/78.02 |
| 6,060,063 | A | 5/2000 | Lansky | |
| 6,242,012 | B1 * | 6/2001 | Newmark et al. | 424/756 |
| 6,391,309 | B1 * | 5/2002 | Empie et al. | 424/757 |
| 6,548,072 | B1 | 4/2003 | Pillai et al. | |
| 6,562,380 | B1 | 5/2003 | Kelly | |
| 6,641,845 | B1 | 11/2003 | Kyrou et al. | |
| 6,750,248 | B2 | 6/2004 | Yong et al. | |
| 6,893,648 | B2 | 5/2005 | Mermelstein et al. | |
| 2003/0104040 | A1 | 6/2003 | Kirby et al. | |
| 2003/0113390 | A1 | 6/2003 | Hole | |
| 2003/0170325 | A1 | 9/2003 | Mermelstein et al. | |
| 2005/0282835 | A1 * | 12/2005 | Villanueva et al. | 514/267 |

FOREIGN PATENT DOCUMENTS

EP 1321149 A1 * 6/2003

OTHER PUBLICATIONS

Ishikawa et al., Massive epistaxis from intracranial extradural aneurysm of the internal carotid artery associated with head injury (author's transl), No shinkei geka. Neurological surgery, (Oct. 1976) vol. 4, No. 10, pp. 953-961.*
Zohar et al., Surgical management of epistaxis in hereditary hemorrhagic Telangiectasia, Archives of otolaryngology—head & neck surgery, (Jul. 1987) vol. 113, No. 7, pp. 754-757.*
Rebeiz et al., Surgical management of life-threatening epistaxis in Osler-Weber-Rendu disease, Annals of plastic surgery, (Aug. 1995) vol. 35, No. 2, pp. 208-213.*

* cited by examiner

*Primary Examiner*—Michele Flood
*Assistant Examiner*—Qiuwen Mi
(74) *Attorney, Agent, or Firm*—Head, Johnson & Kachigian

(57) ABSTRACT

A composition and method for direct application to mucosal membranes, which combines naturally occurring phytoestrogens, such as plant extracts and soy isoflavones, with other active and inactive ingredients in a convenient medium, such as an aqueous cream, aqueous spray or suppository. The composition may be used for the treatment of dry or inadequately hydrated mucosal surfaces, and related complications, such as those affecting the nasal passages or vagina.

9 Claims, No Drawings

TREATMENT OF MUCOSAL MEMBRANES UTILIZING PHYTOESTROGEN

CROSS-REFERENCE TO RELATED APPLICATIONS

This application is a divisional of U.S. patent application Ser. No. 11,379,683, filed Apr. 21, 2006 and claims priority to U.S. Provisional Application No. 60/594,601, filed Apr. 22, 2005, which are incorporated herein by reference.

BACKGROUND OF THE INVENTION

1. Field of the Invention

This invention relates to compositions that are applied directly to mucosal tissue to improve the health thereof and alleviate or eliminate associated complications, and in particularly contemplates a topical cream, solution, gel or suppository that contains phytoestrogens. The disclosed composition is applied directly to any affected or desired mucosal tissue, specifically to the nasal or vaginal mucosal membranes in order to prevent nose bleeds, vaginal dryness and other problems and discomforts related to inadequate hydration or dryness.

2. Prior Art

Mucosal tissue is typically found in orifices of the nasal and rectal passages, the oral cavity and the vagina. Healthy mucosal tissue is moist, and achieving, restoring and/or maintaining proper hydration of these tissues is important. When mucosal tissue is inadequately hydrated, such as may result from a medical or environmental condition. the tissue becomes dry and a person will likely experience some level of inconvenience, pain or discomfort. Commonly encountered complications in the case of nasal passages include epistaxis and rhinorrhagia (nose bleeds), and in the instance of vaginal tissue, dryness and dyspareunia (painful intercourse) may result. Vaginal dryness is often associated with and a recognized complication of menopause and the attendant decrease in a woman's natural hormone levels.

By 2010, an estimated 67 million women in the United States will be above the age of 45, either entering or already in menopause (1). Studies have shown that up to 65% have complaints of vaginal dryness, soreness and pain with intercourse (2,3,4,5). The only treatment that actually alleviates the problem (as opposed to merely treating the symptoms) is vaginal estrogen (6). Vaginal estrogens have also been linked to decreased frequency of urinary tract and bladder infections (7,8) as well as altered vaginal pH which leads to a decreased number of yeast infections (9). Improvements in urinary symptoms such as urinary frequency, urgency and urge incontinence have also been well documented (10). Estrogen receptors have been found on the tissues of the bladder, urethra, and periurethral support tissue (11). Restoring estrogen to the pelvic area increases the tone of these tissues, thereby enhancing urethral closure pressure (which is linked to stress incontinence) (12,13,14), and supports the pelvic organs. Doctors have also recently begun to use vaginal estrogens for interstitial cystitis and other pelvic pain disorders.

Millions of people suffer from chronic recurring nosebleeds in the United States, and epistaxis is responsible for an estimated 450,000 emergency room visits per year (15). The majority of these nosebleeds occur in the anterior (front part) of the nose and are due to dryness, irritation, or trauma. Other than saline nose sprays, to date there have been no other recommended treatments for the prevention of nosebleeds. Certain populations tend to suffer more with anterior nosebleeds, and therefore are easier to include in studies. Patients with hereditary hemorrhagic telangiectasia (HHT, also known as Osler-Weber-Rendau Syndrome) are a case in point, and much research has documented the attempts to decrease the recurrence of nosebleeds in this population. Multiple studies have shown a marked decrease in the severity and number of nosebleeds in this population when treated with estrogens (16-22).

Estrogens (and other steroids) work by binding to nuclear receptors within a cell, and producing a response. Their response can be varied—depending oil the tissue in which they are present. The amount of estrogen needed to effect a desired response has been carefully studied over the years, resulting in some of the estrogen-containing compounds (creams, sprays, ointments, etc.) on the market today. For example, estradiol creams are commonly used to treat the pelvic and vaginal complaints of menopause, and have recently been used to prevent nosebleeds by some otolaryngologists. Recommended dosages have been studied extensively, and are well agreed upon in the literature.

Notwithstanding the efficacy of treating mucosal tissues with human estrogen, it can be appreciated that human estrogen and its derivative therapies are relatively expensive. Animal-derived estrogen compounds are costly as well. It is therefore desirable to provide a composition for treating mucosal membranes that is both effective and inexpensive to produce. Because of their abundance in a variety of plant species distributed around the world, and their well-known estrogenic or pseudoestrogenic character, plant estrogens (phytoestrogens) and related plant compounds are highly desirable alternatives to human or animal estrogen.

Until recently, phytoestrogens had been negatively cast as "alternative" treatments for various ailments such as those associated with menopause, as there was no way of knowing how much phytoestrogen was necessary to effect the same changes as estrogen. Recent studies have been published which quantify the relative binding affinities of estradiol to phytoestrogens, thereby allowing persons skilled in the art to determine exactly how much phytoestrogen is required to make a substance that is bioequivalent to estradiol (23). In the present invention, a natural phytoestrogen composition is disclosed that is bioequivalent to estradiol creams available only by prescription. A variety of plants such as red clover and wild yam contain phytoestrogens or phytoestrogenic compounds that are similar in chemical structure to the estrogens that are present in the human body. Likewise, it is well known in the art that soybeans contain non-steroidal phytoestroen compounds commonly referred to as soy isoflavones. The soy isoflavones, which primarily include daidzen, genistein and glycitein, have been shown to have weak estrogenic activity but have been demonstrated to be beneficial in the treatment of menopausal symptoms.

Black cohosh (*Actaeca racemosa*) is an herb native to North America that is reportedly effective in alleviating menopausal symptoms such as certain of the vasomotor side effects of menopause including irritability, hot flashes, "edginess", and depression (24). Black cohosh has been linked to only very rare adverse effects, and it does not have any significant adverse drug reactions (25). It is thought that black cohosh may stimulate estrogen receptors in humans, but it is unclear whether black cohosh is a true phytoestrogen. This invention is to be distinguished from references disclosing phytoestrogenic nutritional or dietary supplements and those otherwise utilizing phytoestrogenic compounds where such compounds are orally ingested. Persons skilled in the art will appreciate that the route of administration is a key factor, as it bears directly on the timeliness and duration of the relief sought. Likewise, this invention may be distinguished from topical creams for use on the outer skin and epithelial tissues.

It is readily understood by those skilled in the art that mucosal membranes are significantly distinct in both structure and function.

REFERENCES

1. Source: United States Census Bureau—Predictions by Age, Sex, Race and Hispanic Origin
2. Van Geelen J M, van de Weijer P H, Arnolds H T. Urogenital symptoms and resulting discomfort in non-institutionalized Dutch women aged 50-75 years. Int Urogynecol J 2000; 11:9-14.
3. Sarrel P M. Sexuality and menopause. Obstet Gynecol 1990; 76:26 S-30S.
4. Glatt A E, Zinner S H, McCormack W M. The prevalence of dyspareunia. Obstet Gynecol 1990; 75:433-6.
5. Bachmann G A, Leiblum S R, Sandler B, et al. Sexual expression and its determination in the post menopausal woman. Maturitas 1984; 6:19-29.
6. Kaiser, F E. Sexual function and the older woman. Clin Geriatr Med 2003; 19(3): 463-72.
7. Raz R, Stamm W E. A controlled trial of intravaginal estriol in postmenopausal women with recurrent urinary tract infection. N Engl J Med 1993; 329:753-6.
8. Foxman B. An estradiol-releasing vaginal ring delayed the recurrence of urinary tract infection in post-menopausal women. Evidence-based Obstetrics & Gynecology. 2000; 2(1): 19.
9. Nothnagle M. Vaginal estrogen preparations for the relief of atrophic vaginitis. Am Fam Physician. 2004; 69(9): 2111-2.
10. Robinson D. The role of estrogens in female lower urinary tract dysfunction. Urology. 2003; 62(4 Suppl 1): 45-51.
11. Iosif C S. Estrogen receptors in the human female lower urinary tract. Am J Obstet Gynecol. 1981; 141(7): 817-20.
12. Fantl J A, Bump R C, Robinson D, et al: Efficacy of estrogen supplementation in the treatment of urinary incontinence. Obstet Gynecol 88:745, 1996.
13. Fantl J A, Cardozo L, McClish D K, et al: Estrogen therapy in the management of urinary incontinence in postmenopausal women: A meta-analysis. First report of the Hormones and Urogenital Therapy Committee. Obstet Gynecol 83:12, 1994
14. Bhatia N N. Effects of estrogen on urethral function in women with urinary incontinence. Am J Obstet Gynecol. 1989; 160(1): 176-81.
15. Pallin D J, Chng Y M; McKay M P; Emond J A; Pelletier A J; Camargo C A Jr—Ann Emerg Med—1 Jul. 2005; 46(1): 77-81.
16. Cytologic aspects of the nasal respiratory epithelium in postmenopausal women treated with hormone therapy. Caruso S—Fertility and Sterility—1 Mar. 2003; 79(3): 543-9.
17. Estrogen prevention of recurrent epistaxis. Daniell H W—Archives of Otolaryngology—Head and Neck Surgery—1 Mar. 1995; 121(3): 354.
18. [Argon plasma coagulation and topically applied estriol. Long-term results in the treatment of hereditary hemorrhagic telangiectasia of the nasal mucosa.] (German) Sadick H—HMO—February 2033; 51(2): 118-24.
19. Estriol induced squamous metaplasia on the nasal mucosa in patients with hereditary hemorrhagic telangiectasia. Sadick H—Archives of Medical Research—1 Sep. 2005; 36(5): 468-473.
20. Plasma surgery and topical estriol: effects on the nasal mucosa and long-term results in patients with Osler's disease. Sadick H—Otolaryngology—Head and Neck Surgery—1 Sep. 2003; 129(3): 233-8.
21. [Protective effect of daizein on apoptosis cells of nasal mucosa in ovariectomized rats.] (Chinese) Qi BM—Chung-Hue Erh Pi Yen Hou Ko Tsa Chih Chinese Journal of Otorhinolaryngology—1 Feb. 2003; 38(1): 29-31.
22. [Protective effect of purariae isoflavone on apoptosis cells of nasal mucosas in ovariectomized rats] (Chinese) Qi BM—Chung-Kuo Chung Yao Tsa Chih China Journal of Chinese Materia Medica—1 Jun. 2005; 30(11): 855-7.
23. Beck V. Comparison of hormonal activity (estrogen, androgen and progestin) of standardized plant extracts for large scale use in hormone replacement therapy. J Steroid Biochem Mol Biol. 2003; 84(2-3): 259-68.
24. Nesselhut T, Liske E. Pharmacological measures in post-menopausal women with an isopropranolic aqueous extract of *Cimicifuga racemosae* rhizome. Menopause. 1999; 6(4):331.
25. Kligler B. Black cohosh. Am. Fam. Physician. 2003; 68:114-116.

SUMMARY OF THE INVENTION

In general, the invention relates to a composition and method for the treatment of mucosal membranes, such as vaginal and nasal tissue. The composition utilizes plant estrogens known as phytoestrogens from various sources. The composition may also include other herbal supplements, vitamins and/or minerals. Ingredients may be mixed in an aqueous cream or a gel that is applied directly to the mucosal membranes being treated. Alternatively, an aqueous solution of the composition may be either applied or sprayed directly onto a desired or affected mucosal membrane. In yet another embodiment, the composition may be applied by way of suppository.

DETAILED DESCRIPTION OF THE DISCLOSED EMBODIMENTS

The compositions and methods discussed herein are merely illustrative of specific manners in which to make and use the invention and are not to be interpreted as limiting in scope.

While the compositions and methods have been described with a certain degree of particularity, it is to be noted that many modifications may be made in the details of the construction and the arrangement of the composition and methods concentrations and components without departing from the spirit and scope of this disclosure. It is understood that the compositions and methods are not limited to the embodiments set forth herein for purposes of exemplification.

A composition and method for the treatment of mucosal membranes, such as vaginal or nasal tissues, by way of direct application to a person's mucosal membrane. The composition does not include human or animal estrogen but rather utilizes recognized plant estrogens known as phytoestrogens. "Phytoestrogen" as used herein includes known plant estrogens as well as plants, plant compounds and plant products known to have estrogenic effects or possess estrogenic activity. Phytoestrogens may come from any source and may be extracted from common agricultural plants. Those skilled in the art will appreciate that phytoestrogens may be extracted from any suitable plant source. "Extraction" and "extract" refer to any of a number of methods known in the art for handling, preparing and purifying plants and/or plant products, as well as the prepared or purified products.

The composition as disclosed includes 0.1%-5% by weight of extract from the black cohosh herb (*Actaeca racemosa*), which is well known in the art to possess phytoestrogenic effects. Also included in the composition are 0.25%-5% by weight of one or more soybean phytoestrogens known in the art as soy isoflavones. Soy isoflavones may include daidzen, genistein and glycitein. These phytoestrogens may be used alone or in combination with various other compounds. Also included in the composition as disclosed may be 0.01%-2% by weight of vitamin E acetate. So long as phytoestrogens are present is in a biologically active amount, the composition should be suitable for application to mucosal or other endothelial membranes.

The ingredients may be mixed in an aqueous cream or an aqueous solution. A gel or suppository could also be utilized. The cream or gel is to be directly applied to the mucosal membranes being treated. Such application may be achieved using an applicator, a swab or other application device, or merely using one or more fingers. Alternatively, an aqueous solution of the composition may be either applied or sprayed directly onto a mucosal membrane being treated. In yet another embodiment, the composition may be prepared as a suppository. These carriers and routes of administration, and the methods for preparing the same, are well known to those skilled in the art. Selection and preparation of the carrier may vary depending upon intended use, discretion or preference.

In alternative embodiments, the disclosed composition may be admixed with vitamins, minerals, moisturizers, anesthetic agents, antibacterial agents, salts, scented compounds, other herbal supplements or any other materials known in the art to be included in creams or ointments. Persons skilled in the art will recognize that additives of known benefit may be included that will address other complaints, conditions or complications. Such persons will also appreciate that phytoestrogens, as well as other substances that can be mixed with phytoestrogens, should not be over administered, and that the concentration of any of these substances should be tailored to achieve optimal results.

Whereas, it should be understood that other and further modifications, apart from those shown or suggested herein, may be made within the spirit and scope of this invention.

The present invention can be prepared as a water-based cream. An aqueous solution is first assembled using between approximately 3.52% by weight of deionized water, extract of black cohosh (*Actaea racemosa*), and one or more of the commonly recognized isoflavones from the soybean plant (soy isoflavones): daidzein, glycitein and genistein. Methods for preparing and purifying plant extracts are well known to those skilled in the art. Alternatively, commercially prepared and purified extracts are acceptable. An antimicrobial preservative such as Phenonip® (Clariant U.K., Ltd., Leeds, U.K.) is also introduced at this point. This preservative comprises phenoxyethanol, along with one or more parabens selected from the group including the methyl-, butyl-, ethyl-, propyl- and isobutyl variants. In the preferred embodiment, the black cohosh extract is approximately 0.43% by weight, the soy isoflavones are approximately 1.02% by weight, and the total concentration of preservative is approximately 0.04% by weight. The mixture is heated to 180° F. for at least 4 hours. Solids are removed and the resulting solution (the tincture phase) is preserved.

In a separate vessel, the oil phase is prepared using a spreading agent, an additional quantity of an antimicrobial preservative, and a vitamin. The product Myritol 318™ (Cognis, Monheim, Germany), which contains both caprylic and capric triglycerides, is a suitable spreading agent. The spreading agent is preferably 10.00% by weight. An additional 0.75% or so by weight of preservative (such as Phenonip®) is added, along with approximately 0.068% by weight of vitamin E acetate. The addition of a vitamin such as vitamin E is optional. The oil phase is mixed for at least 3 minutes and preserved.

In a separate vessel, 77.71% by weight of deionized water is mixed with the tincture phase, and the resulting solution is mixed for at least 3 minutes. The resulting pH is measured and recorded and this mixture, the water phase, is preserved.

One or more emulsifying agents are mixed with the oil phase for at least 2 minutes, resulting in the emulsification phase. In the preferred embodiment, an emulsifier such as Simulgel 600™ (Seppic, Paris, France) is added at a concentration of approximately 3.22% by weight, and an emulsifier such as Sepigel 305™ (Seppic, Paris, France) is added at a concentration of approximately 3.25% by weight. The water phase is then added to the emulsification phase and the resulting mixture is mixed for at least 15 minutes. Those skilled in the art will recognize that the emulsification phase can be varied depending upon the desired thickness of the composition. The resulting pH of the aqueous cream product is measured and recorded.

The aqueous cream is then packed in convenient packaging. In this embodiment, a single unit package of will consist of approximately 28 days worth of cream. The aqueous cream will preferably be appropriately packaged with instructions for use and perhaps a re-usable applicator if appropriate. The aqueous cream is to be applied by the user or another person directly to the desired or affected areas at regular intervals, preferably once daily, in order to achieve maximum benefit.

The present invention may also be prepared as an aqueous solution, a suppository or a gel. Those skilled in the art will appreciate that the aqueous solution is prepared in a manner similar to the aqueous cream, except that the emulsification and oil phases are modified and/or omitted.

What is claimed is:

1. A method for treatment of nasal mucosal membranes, comprising the steps of:
   providing a composition comprising approximately 0.1% to 5% by weight black cohosh (*Actacea racemosa*), approximately 0.25% to 5% by weight of at least one soy isoflavone and a carrier; and
   administering a therapeutically effective amount of said composition directly to a person's nasal mucosal membranes,
   wherein said treatment of nasal mucosal membranes is for epistaxis or rhinorrhagia caused by, inadequate hydration or dryness.

2. The method of claim 1 wherein said administering is performed at regular intervals.

3. The method of claim 2 wherein said administering is performed daily.

4. The method of claim 1 wherein said at least one soy isoflavone is selected from the group consisting of daidzein, glycitein and genistein.

5. The method of claim 1 wherein said carrier is selected from the group consisting of an aqueous cream, an aqueous solution, and aqueous gel.

6. The method of claim 1 wherein said black cohosh (*Actaea racemosa*) is approximately 0.43% by weight.

7. The method of claim 1 wherein said at least one soy isoflavone is approximately 1.02% by weight.

8. The method of claim 1 wherein said composition further comprises approximately 0.01% to 2% by weight vitamin E acetate.

9. The method of claim 8 wherein said vitamin E acetate is approximately 0.068% by weight.

* * * * *

UNITED STATES PATENT AND TRADEMARK OFFICE
CERTIFICATE OF CORRECTION

PATENT NO. : 7,563,464 B1  Page 1 of 1
APPLICATION NO. : 11/929086
DATED : July 21, 2009
INVENTOR(S) : Bruce Eric Hudkins and Thomas G. Matkov It is certified that error appears in the above-identified patent and that said Letters Patent is hereby corrected as shown below:

Column 2, line 6, change "oil" to --on--.

Signed and Sealed this

Nineteenth Day of January, 2010

David J. Kappos
*Director of the United States Patent and Trademark Office*